United States Patent [19]

Martin et al.

[11] 4,344,934

[45] Aug. 17, 1982

[54] THERAPEUTIC COMPOSITIONS WITH ENHANCED BIOAVAILABILITY

[75] Inventors: Frederick H. Martin, West Chazy; Andrew G. Tsuk, Plattsburgh, both of N.Y.

[73] Assignee: American Home Products Corporation, New York, N.Y.

[21] Appl. No.: 123,143

[22] Filed: Feb. 21, 1980

Related U.S. Application Data

[63] Continuation of Ser. No. 962,435, Nov. 20, 1978, abandoned.

[51] Int. Cl.$^3$ .................. A61K 31/79; A61K 37/00; A61K 31/74; A61K 9/24; A61K 31/245
[52] U.S. Cl. ........................ 424/80; 424/177; 424/78; 424/310; 424/22
[58] Field of Search .................. 424/80, 285, 177

[56] References Cited

U.S. PATENT DOCUMENTS

| | | | |
|---|---|---|---|
| 2,749,274 | 6/1956 | Buckwalter | 424/310 |
| 2,900,304 | 8/1959 | Martin | 167/65 |
| 3,485,914 | 12/1969 | Corn | 424/22 |
| 3,499,959 | 3/1970 | Corn | 424/22 |
| 3,673,163 | 6/1972 | Walkling | 424/80 |
| 3,856,919 | 12/1974 | Rankin | 424/80 |
| 3,881,020 | 4/1975 | Nakamura et al. | 424/80 |
| 3,927,205 | 12/1975 | Ohno et al. | 424/80 |
| 3,980,766 | 9/1976 | Shaw et al. | 424/80 |
| 4,007,258 | 2/1977 | Cohen et al. | 424/80 |
| 4,016,254 | 4/1977 | Seager | 424/80 |
| 4,024,240 | 5/1977 | Thakkar | 424/80 |
| 4,029,782 | 6/1977 | Bornstein | 424/80 |
| 4,029,817 | 6/1977 | Blanco et al. | 424/80 |
| 4,091,091 | 5/1978 | Terrill | 424/80 |
| 4,120,949 | 10/1978 | Bapatla et al. | 424/80 |

FOREIGN PATENT DOCUMENTS

| | | | |
|---|---|---|---|
| 987588 | 4/1976 | Canada | 424/80 |
| 2204425 | 5/1974 | France | 424/78 |
| 2256756 | 8/1975 | France | 424/78 |
| 2285855 | 4/1976 | France | 424/78 |
| 2331327 | 6/1977 | France | 424/78 |
| 810377 | 3/1959 | United Kingdom | 424/80 |
| 1055854 | 1/1967 | United Kingdom | 424/78 |
| 1445995 | 8/1976 | United Kingdom | 424/78 |
| 1456618 | 11/1976 | United Kingdom | 424/78 |
| 1504553 | 3/1978 | United Kingdom | 424/78 |

OTHER PUBLICATIONS

J. Pharm. Science, (1966), vol. 5, 1323, 1324.
Pharm. Ind. 39, (1977), 497–501.
J. of Investigative Dermatology 42, (1964), 197–203.

*Primary Examiner*—Delbert R. Phillips
*Attorney, Agent, or Firm*—Adley F. Mandel

[57] ABSTRACT

Novel compositions comprising wetted mixtures of poorly soluble drugs with water soluble polymers useful in increasing bioavailability are disclosed.

23 Claims, No Drawings

THERAPEUTIC COMPOSITIONS WITH ENHANCED BIOAVAILABILITY

This is a continuation, of application Ser. No. 962,435, filed Nov. 20, 1978, now abandoned.

BACKGROUND OF THE INVENTION

1. Field of the Invention

This invention relates to compositions of poorly soluble or water soluble drugs which provide poor bioavailability or are irregularly absorbed following oral administration of their solid dosage forms. More specifically, the herein disclosed invention relates to new compositions of matter containing poorly soluble or water insoluble drugs, a nontoxic water soluble polymer and a wetting agent. The invention further relates to a process for preparing and a method for using the disclosed compositions which compositions provide a high order of drug bioavailability. In the main, the invention will be illustrated with the known antifungal griseofulvin.

2. Description of the Prior Art

Many drugs give an incomplete and irregular absorption when taken orally, particularly poorly water soluble or water insoluble compounds such as griseofulvin and many steroids. One of the earlier attempts to enhance the availability or bioavailability of such drugs relied on mechanical micronization of the pure compounds in order to decrease their particle size. While micronization did enhance absorption over the use of unmicronized material, absorption of the drug was still incomplete. Further the degree of micronization which can be achieved is limited and the micronized particles tend to agglomerate, thus diminishing both the solubility of the drug and its bioavailability. U.S. Pat. No. 2,900,304 is an illustration of griseofulvin compositions for oral or parenteral administration employing micronized drug particles.

Another approach for attempting to enhance the bioavailability of griseofulvin was studied by Marvel et al and reported in The J'l of Investigative Dermatology, 42, 197–203 (1964). Their studies related to the effect of a surfactant and particle size on the bioavailability of griseofulvin when orally administered. Results of their studies indicated that bioavailability of the drug was enhanced when administered in very dilute solutions or aqueous suspensions. Their results further tended to confirm that enhanced bioavailability was obtained with griseofulvin having a higher specific surface area, at least when administered in full daily divided doses. With respect to the effect of the surfactant sodium lauryl sulfate incorporated into griseofulvin tablets, their results demonstrated some initial enhancement of bioavailability with regularly particle sized drug and very little enhancement with micronized drug in comparison to surfactant-free tablets. These investigators further reported that when the daily dose was divided, the surfactant had no enhancing effect.

Still another approach for the enhancement of drug bioavailability is represented by the work of Tachibana and Nakamura in Kollid-Zeitschrift and Zeitschrift Für Polymere, 203, pgs. 130–133 (1965) and Mayershohn et al in the Journal of Pharmaceutical Science, 55, pgs. 1323–4 (1966). Both publications deal with the use of polyvinylpyrrolidone (PVP) for forming dispersions of a drug. Tachibana discusses the role of PVP in forming very dilute colloidal dispersions of β-carotene in PVP. Mayersohn further prepared solid dispersions or solid solutions of griseofulvin in PVP and the reported results show dissolution rates for the drug increasing with increasing proportions of PVP. This last publication further reported that in the absence of wetting agent in the dissolution medium, the enhancement of the dissolution rate is still greater.

Canadian Pat. No. 987,588 of Riegelman et al, similarly discloses the use and process for making solid dispersions of a drug for enhancing its dissolution rate and bioabailability. In this case the solvents employed were polyethylene glycol (PEG) having molecular weights ranging from 4,000 to 20,000, pentaerythritol, pentaerythritol tetraacetate and monohydrous citric acid. Riegelman postulated that these solvents provided a matrice for griseofulvin which retards crystallization during the solidification process resulting in an ultramicrocrystalline form of the drug with correspondingly faster dissolution. Riegelman's results tend to support this finding of faster dissolution rates for solid solutions of griseofulvin over those of unmicronized, non-wetted micronized and wetted micronized griseofulvin. But his findings were limited to those solid solutions which contain less than 50 percent by weight of the drug since the results demonstrated a slowing of the dissolution rate with higher concentrations of griseofulvin. Riegelman further concluded that the rate of dissolution for a composition having the same ratio of drug to solvent varies significantly depending on the method of preparation, with melt mixing at elevated temperatures in a volatile solvent providing the preferred mode or process.

Another process for preparing ultramicrocrystalline drug particles to increase dissolution of a drug is disclosed by Melliger in Belgian Pat. No. 772,594. That process is characterized by preparing a solution of the drug, PVP and urethane and subsequently removing the urethane. It was reported that, in general, satisfactory results were obtained using solutions in which the quantity of drug represented up to 50 percent by weight of the quantity of PVP present.

U.S. Pat. Nos. 3,673,163 and 4,024,240 respectively are further illustrations relating to the use of PVP in solid dispersions. In the first-cited patent, coprecipitates of acronycine with polyvinylpyrrolidone were prepared in proportions weighted to the polymer to increase the solubility of the coprecipitated acronycine. In the second-cited patent solid antibiotic dispersions containing the antibiotic designated A-32390, in proportions again weighted toward the PVP co-dispersant, were disclosed. Further examples of antibiotic combinations containing PVP are disclosed in U.S. Pat. No. 3,577,514 wherein the PVP is used as a binding agent; and in U.S. Pat. Nos. 3,485,914 and 3,499,959, wherein the PVP is used to sustain the release of the antibiotic. PVP has also been used as a stabilizer with nitroglycerin to retard migration between nitroglycerin tablets as disclosed in U.S. Pat. No. 4,091,091.

With respect to processes employed in preparing certain PVP-griseofulvin compositions, Junginger in Pharm. Ind. 39, Nr. 4 at pgs. 384–388 and Nr. 5 at pgs. 498–501 (1977), reported that spray-dried products provided systems with higher energy levels in comparison with those of simple mixtures and coprecipitates, and correspondingly greater dissolution rates. Junginger further disclosed that the dissolution rates of the simple mixtures were higher when the PVP contents were increased.

In a further attempt to increase the bioavailability of griseofulvin, the drug was treated with small amounts of hydroxypropyl cellulose and formulated into capsules, see Fell et al, J. Pharm. Pharmac., 30, 479–482 (1978). While the formulation produced by this treatment increases the rate and extent of availability of micronized griseofulvin, and authors reported that the treated formulation does not always lead to complete absorption from the upper intenstine as was reported for the Riegelman solid disperse system with polyethylene glycol 6000.

SUMMARY OF THE INVENTION

This invention provides compositions of poorly soluble or water insoluble drugs which provide higher dissolution rates in vitro and increased bioavailability of said drugs in vivo. The composition of this invention comprises a mixture or solution of the drug with a nontoxic, pharmacologically acceptable water soluble polymer wherein said mixture or solution has been treated with a minor amount of a wetting agent selected from anionic and cationic surfactants. The term mixture means the product of a melt mix or that of a dried solution.

Examples of suitable polymers are those selected from at least one of the group comprising polyvinylpyrrolidone, hydroxypropylmethyl cellulose, hydroxypropyl cellulose, methyl cellulose, block copolymers of ethylene oxide and propylene oxide, and polyethylene glycol. Suitable surfactants include those of the anionic variety such as sodium lauryl sulfate, sodium laurate or dioctylsodium sulphosuccinate, and those of the cationic variety such as benzalkonium chloride, bis-2-hydroxyethyl oleyl amine or the like.

In another embodiment, the invention includes a method for treating mammals with said drugs by increasing the bioavailability of the drug following its administration using the composition of this invention.

Still a further embodiment of this invention is a method of preparing compositions with increased bioavailability in mammals from a poorly soluble or water insoluble drug. The method includes the steps of:

(a) Forming a mixture or solution of a drug with a non-toxic, pharmacologically acceptable water-soluble polymer;

(b) drying the drug-polymer solution;

(c) mixing the dried drug-polymer mixture or solution with a surface wetting amount of wetting agent solution wherein said agent is selected from anionic and cationic surfactants; and (d) drying the mixture of step (c).

The method for preparing these compositions is also useful as a method for preparing ultramicrocrystalline griseofulvin.

While the invention is illustrated with poorly soluble or water soluble drugs, and particularly grisefulvin, it will become apparent to those skilled in the art that the compositions and method of this invention are also suitable for other drugs which while relatively soluble have a tendency to agglomerate or crystallize in storage, or after formulation into pharmaceutical dosage forms.

DETAILED DESCRIPTION OF THE INVENTION

This invention relates to compositions of a drug with a water soluble polymer which has been treated with a wetting sufficient amount of a wetting agent selected from anionic and cationic surfactants. In preferred embodiments the composition is a solid, usually a powder, which is then compounded into suitable solid dosage forms for oral administration.

Griseofulvin is a known antibiotic which has been found useful in the treatment of certain fungus diseases of plants, man and animals. Griseofulvin as discussed in the background of this invention is also known as a poorly soluble or water soluble drug, which in vivo provides a low order of bioavailability when administered orally. Thus the composition of the instant invention is particularly useful for griseofulvin and drugs of a similar nature such as certain steroids and antibiotics which due to their low aqueous solubility and/or high melting point are poorly absorbed. Illustrative of such drugs are medrogestone; progesterone; estradiol; 10,11-dihydro-5H-dibenzo[a,d]cycloheptene-5-carboxamide; 5H-dibenzo[a,d]cycloheptene-5-carboxamide and the like. The compositions of this invention, as will soon be appreciated, further permit the formulation of solid dosage forms which may contain high concentrations of the particular drug, such as griseofulvin, with no concomitant loss of bioavailability usually associated with such high concentrations. These compositions thus allow the preparation of elegant solid dosage forms. The compositions of this invention are also resistant to agglomeration of the drug particles or the tendency of the drug in storage to produce undesirable crystal formation which adversely affects bioavailability of the drug.

Polymers useful in this invention include water soluble polymers which are nontoxic and pharmacologically acceptable, particularly for oral administration. Illustrative of polymers, found suitable in this invention include polyvinylpyrrolidone, hydroxypropyl methyl cellulose, hydroxypropyl cellulose, methyl cellulose, block co-polymers of ethylene oxide and propylene oxide, and polyethylene glycol.

Generally these polymers are commercially available over a broad range of average molecular weights. For example, polyvinylpyrrolidone (PVP) is a well known product produced commercially as a series of products having mean molecular weights ranging from about 10,000 to 700,000. Prepared by Reppe's process: 1,4-butanediol obtained in the Reppe butadiene synthesis is dehydrogenated over copper at 200° forming $\gamma$-butyrolactone; reaction with ammonia yields pyrrolidone. Subsequent treatment with acetylene gives the vinyl pyrrolidone monomer. Polymerization is carried out by heating in the presence of $H_2O_2$ and $NH_3$. DeBell et al., German Plastics Practice (Springfield, 1946); Hecth, Weese, Munch. Med. Wochenschr. 1 943, 11; Weese, Naturforschung & Medizin 62, 224 (Wiesbaden 1948), and the corresp vol. of FIAT Review of German Science. Monographs: General Aniline and Film Corp., PVP (New York, 1951); W. Reppe, Polyvinylpyrrolidon (Monographie zu "Angewandte Chemie" no. 66, Weinheim/Bergstr., 1954). Generally available commercial grades have average molecular weights in the range of 10,000 to 360,000, for example, General Aniline and Film Corporation (GAF) markets at least four viscosity grades available as K-15, K-30, K-60, and K-90 which have average molecular weights of about 10,000, 40,000, 160,000 and 360,000, respectively. The K- values are derived from viscosity measurements and calculated according to Fikentscher's formula (Kline, G. M., Modern Plastics 137 No. 1945). Similar commercial products are available from BASF-Wyandotte.

Selection of a particular polymer with its characteristic molecular weight will in part depend on its ability to form suitable dosage forms with the particular drug. Thus, in preparing solid dosages, whether in powder, tablet or capsule units, the composition of this invention should be readily grindable or pulverizable, or in the form of free-flowing powders. A second consideration in the selection of a particular polymer derives from the limitations inherent in the use of specific equipment with polymers of increasingly higher viscosity. For example in forming the drug-polymer solution or mixture, complete dissolution or mixing could be inhibited utilizing blenders, mixer or the like, which are inadequate by reason of low shear or proper baffles to form a uniform and homogeneous drug-polymer solution or mixture. Depending on the process employed for forming of the drug-polymer mixture, another consideration in the selection of a particular polymer is that the polymer be mutually soluble in solvents for the particular drug.

The wetting agents found most suitable for the present invention are those selected from anionic or cationic surfactants. In addition, to those cited in the summary of this disclosure, other suitable surfactants of the anionic variety are illustrated by sodium stearate, potassium stearate, sodium oleate and the like.

The compositions of this invention are prepared in a step by step process.

In the first step, a mixture or solution of the drug witht the water soluble polymer is formed. The mixture can be formed in a solvent or solvent mixture which is a mutual solvent for both the drug and the polymer. Alternatively, the drug-polymer, solvent mixture can, at this stage, be coated onto lactose. Where the drug and the polymer are not subject to degradation at elevated temperatures, the drug-polymer mixture may also be formed by melt mixing. Any volatile solvent in which the drug is soluble is suitable for forming the drug-polymer mixture. For griseofulvin, suitable solvents would include methylene chloride, methylene chloride-ethanol, chloroform, acetone, methyl ethyl ketone and combinations thereof. The most suitable polymer for forming the melt mixture with a drug such as griseofulvin is hydroxypropyl cellulose.

After the drug-polymer mixture or solution has been formed in a solvent it is dried by spray-drying, flash evaporation or air drying. Commercially, spray-drying is most practical since the dried mixture is already in powder form. In the case of the melt mixture drying the drug-polymer mixture is defined as cooling. The melt-mix product is then ground or milled into powder form in preparation for the next step; grinding or milling may also be necessary for dried solvent formed mixtures.

The powdered drug-polymer mixture is then treated with a wetting sufficient amount of a primarily aqueous wetting solution containing a wetting agent selected from anionic and cationic surfactants. This wetting treatment is accomplished by forming a slurry, wet granulation or paste mixture of the powdered drug-polymer with the wetting solution. The wetting solution treatment can be achieved with small incremental additions of the wetting solution or a larger single-shot treatment. The wetting solution treatment apparently fulfills two roles: crystallization of any amorphous regions into ultramicrosize crystals, and the breakup of clusters of such crystals so that they disperse spontaneously when exposed to water. Also, the role of the primarily aqueous solution for the wetting agent treatment is to distribute the wetting agent to surfaces of the drug, whether or not the drug is amorphous or crystalline.

When the employment of more than one polymer is desired, separate drug-polymer mixtures for each polymer are usually prepared which are then initimately blended with each either in dry form prior to or after the wetting solution treatment.

The treated mixture is then dried as earlier described and, if necessary, it is milled, screened or ground prior to formulating into suitable dosage forms with pharmaceutically acceptable excipients.

It will be again appreciated by those skilled in the art that while the invention is illustrated with particularly water insoluble drugs, the composition and method of this invention is also applicable to more soluble drugs in need of enhanced bioavailability. In such instances a broader range of solvents and polymers including the natural gums may be employed to form the drug-polymer mixture.

The concentrations of drug found useful in the drug-polymer mixture of this invention range from the lowest therapeutically effective amount of the drug up to about 90 to 95% of the drug. Thus, in griseofulvin-polymer mixtures, the concentration of griseofulvin ranges from about 0.1% by weight to about 90–95% by weight. In order to form pharmaceutically elegant dosage forms for high dose drugs, the concentration of the drug should be at least 50% by weight of the drug-polymer mixture. In especially preferred embodiments the concentration of drug in the drug polymer mixture will range from about 50% to about 80% by weight.

The required concentration for the wetting agent (or surfactant) in the primarily aqueous wetting solution is a wetting sufficient amount. This amount further depends on whether incremental or single-shot wetting treatments are employed and on whether a slurry or paste treatment is contemplated. Generally, small incremental treatments will require less wetting agent than a larger single shot treatment and a paste treatment will require more wetting agent than a slurry. In any case, it has been found that satisfactory results are obtained when the amount of wetting agent comprises from about 0.025% to about 2.0% by weight of the dried drug polymer mixture and preferrably from about 0.1% or 0.2% to about 1.0% by weight. While higher concentrations of the wetting agent may be satisfactorily employed, no additional advantages in terms of dissolution and/or bioavailability are obtained. It has also been found that when a griseofulvin-polymer, melt mixture has been wetted and crystallized from an aqueous sorbitol solution, enhanced dissolution rates was obtained, however the rate of dissolution was still less that those mixtures treated with a wetting agent.

The invention is further illustrated by the following examples.

EXAMPLE 1

The rate of dissolution of the powdered materials was determined by one of three methods. All three methods gave equivalent results and only the results of method 1 outlined below are used herein unless otherwised noted.

Method (1) A sample containing 20 mg of griseofulvin was dissolved into 1 liter of a 0.02% polysorbate 80 aqueous solution at 37° C. The solution was monitored by a flow cell in a spectrophotometer set at 295 nm.

Method (2) A sample containing 500 mg griseofulvin was dissolved in 10 liters of 0.15% sodium lauryl sulfate in water at 37° C.

Method (3) A sample containing 125 mg griseofulvin was dissolved in 24 liters of water at 37° C.

For examples 2-5 the wetting agent solution employed was as follows: 2.5 g of sodium lauryl sulfate (SLS) were dissolved into 500 ml of a mixture of 100 ml of water and 400 ml of ethyl alcohol or 0.25 g of sodium lauryl sulfate were dissolved into 50 ml of a mixture of 10 ml of water and 40 ml of ethyl alcohol.

EXAMPLE 2

This example describes the preparation of ultramicrocrystalline griseofulvin. The method consists of flash evaporation of a solution containing 10 g of griseofulvin and 10 g of polyvinylpyrrolidone (POVIDONE® K-30, U.S.P.-from GAF Corp.) dissolved in 200 ml of methylene chloride. The evaporation was done on a rotating evaporator at 35°-45° C. in a closed system (Vacuum). About 4-5 ml of the solution to be evaporated was placed in a 100 ml round bottom flask, then placed on the evaporator. Upon evaporation of solvent, the material was deposited onto the wall of the flask. The dried material was found to be amorphous by X-ray diffraction. Next, this amorphous material was treated with the SLS solution. To 2 g of powder, 0.125 ml of the solution was added with constant mixing and the solvent was allowed to dry. This was repeated six more times until a total of 0.875 ml of solution had been added. Microscopic observation and dissolution data showed that ultramicrocrystalline griseofulvin was formed by this method and has a much faster dissolution rate into water at 37° C., than microsized griseofulvin or untreated amorphous material

TABLE 1

Dissolution profile of griseofulvin into water at 37° C. The dissolved griseofulvin, unless otherwise specified, is expressed in mg/liter over an elapsed time period in minutes.

| Sample | 1 min. | 2 min. | 3 min. | 5 min. | 10 min. | 14 min. |
|---|---|---|---|---|---|---|
| 1 | 11.2 | 11.7 | 11.9 | 12.0 | 12.2 | 12.5 |
| 2 | 2.5 | 3.8 | 4.8 | 6.5 | 8.7 | 9.8 |
| 3 | 1.6 | 2.7 | 3.4 | 4.7 | 7.0 | 8.2 |

1-Flash evaporated griseofulvin: PVP (50% griseofulvin) treated with SLS solution.
2-Flash evaporated griseofulvin: PVP(50% griseofulvin)
3-Microsized griseofulvin

EXAMPLE 3

Table 1—This example describes the preparation of ultramicrocrystalline griseofulvin by coating a solution of griseofulvin and polyvinylpyrrolidone onto lactose then treating the powder with a solution of sodium lauryl sulfate.

A solution was prepared by dissolving 1 g of griseofulvin and 1 g of polyvinylpyrrolidone into 8 ml of methylene chloride. All this solution was coated successively in 1 ml portions onto 2 g of lactose and allowed to dry. The material formed by this method was crystalline by X-ray diffraction. Next 1 ml of the SLS solution was added to the 4 g powder and allowed to dry. Microscopic observation and dissolution data showed that the griseofulvin formed by this method was ultramicrocrystalline and had a much faster dissolution rate into water at 37° C., than microsized griseofulvin.

TABLE 2

| Sample | 1 min. | 2 min. | 3 min. | 5 min. | 10 min. | 14 min. |
|---|---|---|---|---|---|---|
| 1 | 10.8 | 11.6 | 11.8 | 11.9 | 12.0 | 12.0 |
| 2 | 7.0 | 8.7 | 9.7 | 10.5 | 11.5 | 11.5 |
| 3 | 1.6 | 2.7 | 3.4 | 4.7 | 7.0 | 8.2 |

1-griseofulvin: PVP (50:50) coated onto lactose and treated with SLS solution.
2-griseofulvin: PVP (50:50) coated onto lactose.
3-Microsized griseofulvin

EXAMPLE 4

This example describes the preparation of ultramicrocrystalline griseofulvin by spray drying a solution of griseofulvin and polyvinylpyrrolidone then treating with powder with a solution of sodium lauryl sulfate. A solution of 50 g of griseofulvin and 50 g of polyvinylpyrrolidone dissolved in 2 liters of methylene chloride was spray dried at room temperature. A mixture of 1 ml of the SLS solution and 2 g of the powder was dried. Microscopic observation and dissolution data showed the griseofulvin formed by this method to be ultramicrocrystalline and has a much faster dissolution rate into water at 37° C. than microsized griseofulvin.

TABLE 3

| Sample | 1 min. | 2 min. | 3 min. | 5 min. | 10 min. | 14 min. |
|---|---|---|---|---|---|---|
| 1 | 10.5 | 10.7 | 10.8 | 11.0 | 11.0 | 11.0 |
| 2 | 3.2 | 4.4 | 5.6 | 8.1 | 9.9 | 10.4 |
| 3 | 1.6 | 2.7 | 3.4 | 4.7 | 7.0 | 8.2 |

1-Spray dried griseofulvin: PVP (1:1) treated with SLS solution.
2-Spray dried griseofulvin: PVP(1:1)
3-Microsized griseofulvin

EXAMPLE 5

This example describes preparation of ultramicrocrystalline griseofulvin by spray drying a solution of griseofulvin and polyvinylpyrrolidone and then treating the powder with a solution of sodium lauryl sulfate. A solution containing 70 g of griseofulvin and 30 g of polyvinylpyrrolidone dissolved into 2 liters of methylene chloride was spray dried at room temperature. To 2 g of the powder, ¾ ml of the SLS solution was added in six 0.125 ml increments and dried between additions. Microscopic observation and dissolution data showed that the griseofulvin formed by this method was ultramicrocrystalline and had a much faster dissolution rate into water at 37° C. than microsized griseofulvin.

TABLE 4

| Sample | 1 min. | 2 min. | 3 min. | 5 min. | 10 min. | 14 min. | 15 min. |
|---|---|---|---|---|---|---|---|
| 1 | 10.0 | 10.9 | 11.5 | 12.0 | 12.5 | 12.7 | — |
| 2 | 2.5 | 3.9 | 4.9 | 6.5 | 9.0 | 10.4 | — |
| 3 | 1.6 | 2.7 | 3.4 | 4.7 | 7.0 | 8.2 | — |
| 4 | 1.9 | 3.5 | 4.6 | 6.3 | 8.6 | — | 9.7 |
| 5 | 1.8 | 3.0 | 4.0 | 5.8 | 8.1 | — | 9.3 |
| 6 | 1.9 | 3.1 | 4.3 | 6.0 | 8.6 | — | 9.7 |

1-Spray dried griseofulvin: PVP(70:30) treated with SLS solution.
2-Spray dried griseofulvin: PVP(70:30).
3-Microsized griseofulvin
4-Spray-dried griseofulvin: PVP treated with the non-ionic polysorbate 80. griseofulvin: PVP: non-ionic(69.7:29.7:0.5)
5-Spray dried griseofulvin: PVP treated with the non-ionic block co-polymer of ethylene oxide and propylene oxide (Pluronic® F77) griseofulvin:PVP: non-ionic (69.7:29.7:0.5)
6-Spray dried griseofulvin: PVP treated with the non-ionic isooctyl phenoxy polyethoxy ethanol.griseofulvin PVP: non-ionic (69.7:29.7:0.5)

TABLE 5

| Sample | Dissolution Profile | | | | | |
|---|---|---|---|---|---|---|
| | 1 min. | 2 min. | 3 min. | 5 min. | 10 min. | 14 min. |
| 1 | 10.0 | 10.9 | 11.5 | 12.0 | 12.5 | 12.7 |
| 2 | 6.9 | 8.7 | 9.7 | 10.4 | 11.3 | — |
| 3 | 6.0 | 7.0 | 7.3 | 7.7 | 8.0 | — |
| 4 | 1.6 | 2.7 | 3.4 | 4.7 | 7.0 | 8.2 |

1-Spray dried griseofulvin: PVP(70:30) treated SLS
2-Dorsey Laboratories' Gris-Peg (Trademark) for griseofulvin composition in PEG 6000.
3-Schering Laboratories' Fulvicin P/G (Trademark) for griseofulvin composition in PEG 6000.
4-Microsized griseofulvin.

EXAMPLE 6

In the samples evaluated in Tables 6–8, the following further describes their preparation.

MATERIALS & METHODS

Two grades of hydroxypropyl cellulose were used, Klucel ® EF and Klucel ® LF (Hercules), the former preferred for its lower viscosity. Coarse griseofulvin, spray dried lactose, sorbitol, and sodium lauryl sulfate were the other ingredients. The solvents were methylene chloride and absolute ethanol, U.S.P. grade.

Crystallinity of griseofulvin preparations were judged by visual microscopic observation under crossed polarizers, or by X-ray diffraction assay.

Preparation of a Melt Mixture

A glass melting tube immersed in a hot oil bath was used to melt together various amounts of griseofulvin and Klucel. After complete melting and mixing, the liquid mixture was rapidly chilled under a cold water tap, while rotating the tube horizontally so as to distribute the liquid over the inside walls. After solidification, the tube was further cooled in a dry ice bath, which fractured the product and allowed its removal from the glass tube. The chunky product was ground to a powder in a micromill.

Crystallization with a Sorbitol Solution

Typically, an amount of powdered melt mixture was intimately mixed with an equal weight of an aqueous solution containing, by weight, about 22% sorbitol and 13% ethanol. This was vigorously mixed and worked with a spatula, until the doughy mixture acquired the consistency of a smooth cream or paste. The paste was allowed to dry, and the dry chunky product was ground in a mortar.

Spray Dried Mixtures

Solution for spray drying were prepared by dissolving griseofulvin and Klucel in a mixture of methylene chloride and ethanol. An Anhydro Laboratory Spray Dryer No. 3 was used, and the solution was spray dried at room temperature.

Crystallization with a Sodium Lauryl Sulfate Solution

Typically, a weight of spray dried powder (whether amorphous or crystalline) was intimately mixed with about 0.9 weight of a 1.5% aqueous solution of sodium lauryl sulfate. The solution could also contain ethanol and sorbitol or lactose, but this was found to be unnecessary. The doughy mixture was vigorously mixed and worked with a spatula, until it became a smooth paste. Then, about 0.25 weight of lactose was added, and mixed until again smooth. The paste was spread and dried at around 85° C. The elevated temperature coagulated the wet paste into granules, which could be stirred and mixed at times during drying, to diminish caking. The dry product was milled and passed through a 60 or 80 mesh screen. The product contained about 1% sodium lauryl sulfate.

Treatment of Spray Dried Mixtures with Sodium Lauryl Sulfate Solution, Without Pasting About 2.0 g of spray dried griseofulvin-Klucel ® mixture was placed in a mortar, then treated successively with six 0.125 ml portions of a wetting solution, allowing enough drying between portions to prevent the powder from becoming pasty. The wetting solution contained 5 mg/ml sodium lauryl sulfate in a mixture of 4 parts ethanol -1 part water, by volume. The final granular powder contained about 0.2% sodium lauryl sulfate.

Scale-up Attempts of Paste Treatment

Crystallization of spray dried powders with sodium lauryl sulfate solution on a 1 kg scale were achieved in a Hobart mixer, equipped with a small bowl and a pastry blade. Lactose was added to the paste, then the mixture was spread on trays and dried at 85° C. The chunky, partially caked product was milled and screened.

Spray Dried Mixtures of Griseofulvin & Hydroxypropyl cellulose (Klucel) ®

| Composition of Solution | | | |
|---|---|---|---|
| Solids Content (g/l of solvent) | Griseofulvin Content (% of Solids) | Solvent Volume Ratio (MeCl$_2$/EtOH) | Crystallinity of Product |
| 100 | 50 | 7/1 | Mostly amorphous |
| 50 | 75 | 9/1 | Amorphous |
| 167 | 75 | 8.6/1 | Crystalline |
| 200 | 80 | 7/1 | Crystalline |

TABLE 6

| Sample | Dissolution profile. | | | | | | |
|---|---|---|---|---|---|---|---|
| | 1 min. | 2 min. | 3 min. | 5 min. | 10 min. | 15 min. | 20 min. |
| 1 | 4.1 | 8.0 | 9.2 | 10.8 | 12.6 | 13.4 | 13.7 |
| 2 | 1.5 | 2.7 | 3.4 | 4.7 | 7.0 | 8.4 | 9.2 |
| 3 | 0.5 | 1.0 | 1.3 | 2.0 | 3.2 | 4.2 | 5.0 |

1-Melt mixture of griseofulvin (75%)-Klucel ® (25%), crystallized with a sorbitol solution
2-Micronized griseofulvin
3-Melt mixture of griseofulvin (83%)-Klucel ® (17%), amorphous.

TABLE 7

| Sample | 1 min. | 2 min. | 3 min. | 5 min. | 10 min. | 15 min. | 20 min. |
|---|---|---|---|---|---|---|---|
| 1 | 2.0 | 3.6 | 4.7 | 6.5 | 9.8 | 11.4 | 12.8 |
| 2 | 2.0 | 3.6 | 4.7 | 6.5 | 9.2 | 10.5 | 11.8 |
| 3 | 1.5 | 2.7 | 3.4 | 4.7 | 7.0 | 8.4 | 9.2 |
| 4 | 0.8 | 1.5 | 2.0 | 2.8 | 4.7 | 5.8 | 6.5 |

1-Spray dried griseofulvin (75%)-Klucel ® (25%) mixture, amorphous.
2-Spray dried griseofulvin (50%)-Klucel ® (50%) mixture, mostly amorphous.
3-Micronized griseofulvin.
4-Spray dried griseofulvin (80%)-Klucel ® (20%) mixture crystalline.

TABLE 8

| Sample | 1 min. | 2 min. | 3 min. | 5 min. | 10 min. | 15 min. | 20 min. |
|---|---|---|---|---|---|---|---|
| 1 | 6.2 | 11.1 | 11.5 | 12.0 | 12.5 | 12.7 | 12.8 |
| 2 | 6.2 | 10.2 | 11.0 | 11.6 | 12.1 | 12.2 | 12.3 |

TABLE 8-continued

| Sample | 1 min. | 2 min. | 3 min. | 5 min. | 10 min. | 15 min. | 20 min. |
|---|---|---|---|---|---|---|---|
| 3 | 1.5 | 2.7 | 3.4 | 4.7 | 7.0 | 8.4 | 9.2 |

1-Spray dried mixture of griseofulvin: PVP (70:30), treated with SLS solution./
2-Spray dried mixture of griseofulvin: Klucel ® (75:35), crystallized with sodium lauryl sulfate solution.
3-Micronized griseofulvin

EXAMPLE 7

This example describes preparation of ultramicrocrystalline griseofulvin by spray drying a solution of griseofulvin and hydroxypropyl methyl cellulose and then treating the powder with a solution of sodium lauryl sulfate. A solution containing 40 g of hydroxypropyl methylcellulose 80 g of griseofulvin and 200 ml of Methanol dissolved into 2 liters of methylene chloride was spray dried at R.T. The dried material was found to be amorphous by X-ray diffraction. To 4 g of the powder, 4 ml of a solution containing 1.5 g sodium lauryl sulfate dissolved into 100 ml of $H_2O$ was mixed in, and then dried. Microscopic observation and dissolution data shows that ultramicrocrystalline griseofulvin was formed by this method and has a much faster dissolution rate into water at 37° C., then microsized griseofulvin or untreated amorphous material.

EXAMPLE 8

This example describes preparation of ultramicrocrystalline griseofulvin by spray drying a solution of griseofulvin and methylcellulose and then treating the powder with a solution of sodium lauryl sulfate. A solution containing 40 g of methylcellulose (15 cps) and 120 g of griseofulvin, and 200 ml of methanol dissolved into 2 liters of methylene chloride was spray dried at R.T. The dried material was found to be partly amorphous and partly crystalline by x-ray diffraction. To 4 g of the powder, 4 ml of a 1.5% sodium lauryl sulfate solution was added and mixed in. The mixture then was dried. Microscopic observation and dissolution data shows that ultramicrocrystalline griseofulvin was formed by this method, and it has a much faster dissolution rate then microsized griseofulvin or untreated material.

EXAMPLE 9

This example describes preparation of ultramicrocrystalline griseofulvin by spray drying a solution of griseofulvin and poly(oxypropylene) poly(oxyethylene) block copolymer (Pluronic ® F77 BASF Wyandotte Corp.) and then treating the powder with a solution of sodium lauryl sulfate. A solution containing 100 g of the block copolymer and 100 g griseofulvin dissolved into 2 liters of methylene chloride was spray dried at RT, to 4 g of the powder, 2 ml of a 1.5% sodium lauryl sulfate was added, mixed and then dried. Microscopic observation and dissolution data shows that ultramicrocrystalline griseofulvin was formed by this method, and it has a faster dissolution rate then microsized griseofulvin or untreated material.

EXAMPLE 10

This example describes preparation of ultramicrocrystalline griseofulvin by spray drying a solution of griseofulvin and polyethylene glycol and then treating the powder with a solution of sodium lauryl sulfate. A solution containing 100 g of griseofulvin and 100 g of polyethylene glycol 6000 dissolved into methylene chloride was spray dried. To 4 g of the powder, 2 ml of a 1.5% sodium lauryl sulfate solution was added, mixed and dried. Microscopic observation and dissolution data shows that ultramicrocrystalline griseofulvin was formed by this method, and it has a much faster dissolution rate then microsized griseofulvin or untreated material.

EXAMPLE 11

This example describes preparation of ultramicrocrystalline griseofulvin by spray drying a solution containing griseofulvin and hydroxypropyl methylcellulose and then treating the powder with a solution of sodium lauryl sulfate. A solution containing 40 g of hydroxypropyl methylcellulose, 160 g of griseofulvin and 100 ml of ethanol dissolved into 2 liters of methylene chloride was spray dried. To 2 g of powder, 0.125 ml of sodium lauryl sulfate wetting solution (see above example No. 7) was added with constant mixing and the solvent was allowed to dry. This was repeated five more times until a total of 0.750 ml of solution had been added. Microscopic observation and dissolution data shows that ultramicrocrystalline griseofulvin was formed by this method and it has a much faster dissolution rate then microsized griseofulvin or untreated material.

EXAMPLE 12

This example describes preparation of ultramicrocrystalline griseofulvin by spray drying a solution of griseofulvin and polyvinylpyrrolidone and then treating the powder with a solution of benzalkonium chloride. A solution of 70 g of griseofulvin and 30 g of polyvinylpyrrolidone dissolved into 2 liters of methylene chloride was spray dried at RT. To 4 g of the powder, 2 ml of a 1% aqueous solution of benzalkonium chloride was added, mixed and then dried. Microscopic observation and dissolution data shows that ultramicrocrystalline griseofulvin was formed by this method, and it has a much faster dissolution rate then microsized griseofulvin or untreated material.

EXAMPLE 13

This example describes preparation of ultramicrocrystalline griseofulvin by spray drying a solution of griseofulvin and polyvinylpyrrolidone and then treating the powder with a solution of sodium laurate. A solution of 70 g of griseofulvin and 30 g of polyvinylpyrrolidone dissolved into 2 liters of methylene chloride was spray dried at RT. To 4 g of the powder, 2 ml of a 2% aqueous solution of sodium laurate was added, mixed and then dried. Microscopic observation and dissolution data shows that ultramicrocrystalline griseofulvin was formed by this method, and it has a much faster dissolution rate then microsized griseofulvin or untreated material.

EXAMPLE 14

This example describes preparation of ultramicrocrystalline griseofulvin by spray drying a solution of griseofulvin and polyvinylpyrrolidone and then treating the powder with a solution of dioctyl sodium sulfosuccinate. A solution of 70 g of griseofulvin and 30 g of polyvinylpyrrolidone dissolved into 2 liters of methylene chloride was spray dried at RT. To 4 g of the powder, 2 ml of a 1% aqueous solution of dioctyl sodium sulfosuccinate was added, mixed and then dried. Microscopic observation and dissolution data shows that ultramicrocrystalline griseofulvin was formed by this method, and it has a much faster dissolution rate then microsized griseofulvin or untreated material.

EXAMPLE 15

This example describes preparation of ulramicrocrystalline griseofulvin by spray drying a solution of griseofulvin and polyvinylpyrrolidone and then treating the powder with a solution of bis(2-hydroxyethyl)oleylamine. A solution of 70 g of griseofulvin and 30 g of polyvinylpyrrolidone dissolved into 2 liters of methylene chloride was spray dried at RT. To 4 g of the powder, 2 ml of a 2% aqueous solution of bis(2-hydroxyethyl)oleylamine was added, mixed and then dried. Microscopic observation and dissolution data shows that ultramicrocrystalline griseofulvin was formed by this method, and it has a much faster dissolution rate then microsized griseofulvin or untreated material.

viding maximum bioavailability or absorption following oral administration.

The results indicated that there were no statistically significant differences between the 3 dosage forms evaluated.

The cumulative mean for all groups expressed in mg of either free or total 6-DMG found in the urine for each of the three dosages was as follows:

|  | Gris-PVP | | Gris-hydroxypropyl cellulose | | Marketed Product | |
| --- | --- | --- | --- | --- | --- | --- |
|  | Free | Total | Free | Total | Free | Total |
| 0–24 hours | 48.6 | 75.8 | 50.3 | 81.1 | 48.9 | 76.7 |
| 24–48 hours | 19.1 | 30.0 | 20.7 | 33.3 | 19.5 | 37.1 |
| 0–48 hours | 68.7 | 105.8 | 71.0 | 114.4 | 68.4 | 113.8 |

TABLE 9

The results of dissolution studies on the samples prepared by Examples 7–15 are listed below. The unit of expression for this Table is percent of saturation achieved in time expressed in minutes.

| Polymer | Wetting agent | wt. % Polymer | Wetting Agent | Griseofulvin | Percent of Saturation - time Min. | | | | | | | | |
| --- | --- | --- | --- | --- | --- | --- | --- | --- | --- | --- | --- | --- | --- |
|  |  |  |  |  | 1 | 2 | 3 | 4 | 5 | 10 | 15 | 20 | 25 |
| None-Griseofulvin Microsized | None | None | None | 100% | 14.8 | 22.3 | 30.3 | 36.8 | 42.6 | 64.5 | 76.1 | 83.1 | 86.5 |
| Polyvinylpyrrolidone | Sodium Lauryl Sulfate | 49.9 | 0.2 | 49.9 | 92.9 | 99.2 | 100.6 | 101.3 | 101.9 |  |  |  |  |
| Polyvinylpyrrolidone | Sodium Lauryl Sulfate | 29.9 | 0.2 | 69.9 | 91.6 | 97.0 | 98.8 | 99.4 | 99.6 | 100.0 |  |  |  |
| Polyvinylpyrrolidone | Sodium Lauryl Sulfate | 9.9 | 0.2 | 89.9 | 60.7 | 70.0 | 89.0 | 83.9 | 85.8 | 91.6 | 93.5 | 94.8 | 95.6 |
| Polyvinylpyrrolidone | Benzalkonium Chloride | 29.8 | 0.5 | 69.7 | 75.7 | 87.2 | 92.6 | 95.3 | 97.0 | 99.3 | 100 |  |  |
| Polyvinylpyrrolidone | Dioctyl Sodium Sulfosaccinate | 29.8 | 0.5 | 69.7 | 86.5 | 92.9 | 95.5 | 96.8 | 97.4 | 98.3 | 99.8 |  |  |
| Polyvinylpyrrolidone | Sodium Laurate | 29.7 | 1.0 | 69.3 | 53.5 | 65.2 | 72.3 | 77.4 | 81.9 | 90.3 | 94.8 |  |  |
| Polyvinylpyrrolidone | Bis(2-Hydroxyethyl) Oleyl Amine | 29.7 | 1.0 | 69.3 | 74.2 | 83.9 | 88.6 | 91.6 | 93.2 | 97.4 | 100.00 | 100.6 |  |
| Hydroxypropyl Cellulose | Sodium Lauryl Sulfate | 24.9 | 0.2 | 74.9 | 85.4 | 93.2 | 96.7 | 98.3 | 99.3 | 101.9 |  |  |  |
| Hydroxypropyl Cellulose | Sodium Lauryl Sulfate | 19.9 | 0.2 | 79.9 | 61.9 | 71.6 | 77.4 | 81.5 | 84.5 | 94.2 | 99.4 | 101.9 | 109.0 |
| Hydroxypropyl Methyl Cellulose | Sodium Lauryl Sulfate | 32.8 | 1.5 | 65.8 | 36.8 | 49.0 | 57.4 | 69.8 | 67.7 | 88.4 | 101.3 | 108.4 | 112.9 |
| Polyethylene Glycol | Sodium Lauryl Sulfate | 49.6 | 0.7 | 99.6 | 71.2 | 83.2 | 89.6 | 92.9 | 94.5 | 98.3 | 99.4 | 99.6 |  |
| Polyoxyethylene Polyoxypropylene Copolymer | Sodium Lauryl Sulfate | 44.6 | 0.7 | 49.6 | 43.2 | 56.7 | 63.8 | 68.6 | 72.3 | 81.3 | 85.4 | 87.7 | 89.0 |

*Saturation 11.6 mg liter.

EXAMPLE 16

The relative bioavailability of the composition of this invention with two different polymer mixtures and that of one marketed ultramicrosize griseofulvin dosage form was studied in humans.

The urinary excretion of the major griseofulvin metabolite 6-Desmethyl griseofulvin (6-DMG) was determined for all three dosage forms following the administration of 250 mg of griseofulvin (in the form of 125 mg tablets) to 15 healthy adult volunteers divided into three groups using a crossover experimental design. The total tablet weight for each of the 125 mg dosages was 350 mg. The compositions of the invention were represented by spray dried griseofulvin mixtures with either polyvinylpyrrolidone or hydroxypropyl cellulose both treated with SLS. The marketed product evaluated was Schering's Fulvicin ® P/G which is perceived as pro- In a second bioavailability study conducted with 4 healthy adult volunteers, dosage forms containing 500 mg of micronized griseofulvin were administered in the form of a single tablet or 2 capsules each containing 250 mg of micronized griseofulvin. Since griseofulvin is not a dose dependent drug, twice the amount of the 6-DMG metabolite should be excreted over that of a 250 mg dosage of griseofulvin.

The cumulative mean was as follows:

|  | 500mg Griseofulvin Tablet | | 500mg Griseofulvin as 2 × 250mg capsules | |
| --- | --- | --- | --- | --- |
|  | Free | Total | Free | Total |
| 0–24 hours | 34.4 | 35.5 | 38.0 | 54.7 |
| 24–48 hours | 63.5 | 104.2 | 64.4 | 102.8 |
| 0–48 hours | 97.9 | 157.9 | 102.4 | 157.5 |

EXAMPLE 17

Typical direct compression tablet formulations may be prepared as follows for 125 mg dosage forms having a final tablet weight of 350 mg.

| A. | 1. Griseofulvin at 59.5% in mixture with hydroxypropyl cellulose, SLS treated | 210.0 g |
|---|---|---|
| | 2. Microcrystalline Cellulose | 87.0 g |
| | 3. Lactose, Edible | 32.0 g |
| | 4. Sodium Starch Glycolate | 17.5 g |
| | 5. Magnesium Stearate U.S.P. | 3.5 g |
| | Theoretical Tablet Weight | 350 mg. |
| B. | 1. Griseofulvin at 67.5% in PVP mixture treated with SLS | 185.0 g |
| | 2. Microcrystalline Cellulose | 87.0 g |
| | 3. Lactose, Edible | 67.0 g |
| | 4. Sodium Starch Glycolate | 17.5 g |
| | 5. Magnesium Stearate | 3.5 g |
| | Theoretical Tablet Weight | 350 g |

In both A and B, ingredients 1–4 were blended together until uniform, passed through a screen, blended with ingredient 5 and compressed at the correct tablet weight.

The dissolution profile for the compressed tablets demonstrated further that there was no significant difference in dissolution for the formulated tablet as compared with the unformulated powdered material.

What is claimed is:

1. A pharmaceutical composition in dry solid form comprising a mixture of a therapeutically effective amount of a poorly water soluble drug and a non-toxic, pharmacologically acceptable, water-soluble polymer; said mixture being the product of a melt mix or of a dried solution and said mixture in dry solid form having been treated with solution comprising water and a minor amount of a wetting agent selected from anionic and cationic surfactants and then dried.

2. The composition of claim 1 wherein said polymer is selected from at least one of polyvinylpyrrolidone, hydroxypropylmethyl cellulose, hydroxypropyl cellulose, methyl cellulose, block co-polymers of ethylene oxide and propylene oxide, and polyethylene glycol.

3. The composition of claim 1 wherein said wetting agent is an anionic surfactant selected from sodium lauryl sulfate, sodium laurate, dioctylsodium sulfosuccinate, sodium stearate, potassium stearate and sodium oleate.

4. The composition of claim 1 wherein said wetting agent is a cationic surfactant selected from benzalkonium chloride and bis-2-hydroxyethyl oleyl amine.

5. The composition of claim 1 or 2 wherein the concentration of said drug is from about 0.1% to about 95% by weight and the concentration of said polymer is from about 5% to about 99% by weight.

6. The composition of claim 1 or 2 wherein the concentration of said drug is from about 50% to about 90% by weight and the concentration of said polymer is from about 10% to about 50% by weight.

7. The composition of claim 1 or 2 wherein the concentration of said drug is about 50% to about 80% by weight and the concentration of said polymer is from about 20% to about 50% by weight.

8. The composition of claim 1, 2, 3 or 4 wherein the concentration of the wetting agent in the drug-polymer mixture is from about 0.025% to about 2.0% by weight.

9. The composition of claim 1, 2, 3 or 4 wherein the concentration of the wetting agent in the drug-polymer mixture is from about 0.2% to about 1.0% by weight.

10. The composition of claim 1, 2 3 or 4 wherein said drug is griseofulvin.

11. The composition of claim 1, 2, 3 or 4 wherein said drug is griseofulvin in a concentration ranging from about 0.1% to about 90% by weight; the concentration of the polymer is from about 5% to about 95% by weight; and the concentration of the wetting agent in the drug-polymer mixture is from about 0.025% to about 2.0% by weight.

12. The composition of claim 1, 2, 3 or 4 wherein said drug is griseofulvin in a concentration ranging from about 50% to about 80% by weight; the concentration of the polymer is from about 20% to about 50% by weight; and the concentration of the wetting agent in the drug-polymer mixture is from about 0.2% to about 1.0% by weight.

13. A pharmaceutical composition in solid form comprising a mixture of at least about 0.1% to about 90% by weight of griseofulvin; from about 5% to about 95% by weight of a polymer selected from polyvinylpyrrolidone, hydroxypropyl methyl cellulose, hydroxypropyl cellulose, methyl cellulose, block copolymers of ethylene oxide and propylene oxide, and polyethylene glycol; and from about 0.025% to about 2.0% by weight of a wetting agent selected from anionic surfactants which was added to the drug-polymer mixture in dry solid form by a wet treatment from a solution comprising water; wherein said drug polymer mixture is the product of a melt mix or of a dried solution and said composition was dried following the wet treatment.

14. The composition of claim 13 wherein the concentration of the griseofulvin is from about 50% to about 80% by weight; from about 20% to about 50% by weight of a polymer selected from polyvinylpyrrolidone and hydroxypropyl cellulose; and from about 0.2% to about 1.0% by weight of an anionic surfactant selected from sodium lauryl sulfate, sodium sulfate and dioctylsodium sulfosuccinate.

15. A compressed pharmaceutical tablet comprising the composition of claim 1, 2, 3, 4, 13 or 14 wherein said drug is in the form of ultramicrocrystals and pharmaceutically acceptable excipients.

16. A method of preparing a pharmaceutical composition with increased bioavailability in mammals from a poorly water soluble or water insoluble drug, which comprises:
   (a) forming a solution of the drug with a pharmacologically acceptable, water soluble polymer;
   (b) drying the drug-polymer solution;
   (c) treating the dried drug-polymer solution with a wetting sufficient amount of a solution comprising water and a wetting agent selected from anionic and cationic surfactants; and
   (d) drying the mixture of step (c).

17. The method of claim 16 wherein said polymer is selected from polyvinylpyrrolidone, hydroxypropyl cellulose, hydroxypropylmethyl cellulose, methyl cellulose, polyethylene glycol and block co-polymers of ethylene oxide and propylene oxide and said wetting agent is an anionic surfactant selected from sodium lauryl sulfate, sodium laurate and dioctyl sodium sulfosuccinate.

18. The method of claim 16 or 17 wherein the solution of the drug and polymer is formed in a mutual solvent; the drug is griseofulvin and wherein the concentration of griseofulvin in the dried mixture of step (d) is from about 0.1% to about 90% by weight and the concentration of the wetting agent in the dried mixture is about 0.025–2.0% by weight.

19. The method of claim 18 wherein the grisefulvin concentration is from about 50% to about 80% and the concentration of said wetting agent is from about 0.2% to about 1.0%.

20. The product prepared by the method of claim 16 or 17.

21. A method for treating fungal diseases in mammals which comprises orally administering to said mammal the composition of claim 13 or 14.

22. The product prepared by the method of claim 18.

23. The product prepared by the method of claim 19.

* * * * *